United States Patent [19]

Shallman

[11] Patent Number: 5,403,328
[45] Date of Patent: Apr. 4, 1995

[54] SURGICAL APPARATUS AND METHOD FOR SUTURING BODY TISSUE

[75] Inventor: Richard W. Shallman, Richland, Wash.

[73] Assignee: United States Surgical Corporation, Norwalk, Conn.

[21] Appl. No.: 13,244

[22] Filed: Feb. 3, 1993

Related U.S. Application Data

[63] Continuation of Ser. No. 872,212, Apr. 22, 1992, abandoned.

[51] Int. Cl.⁶ .............................................. A61B 17/00
[52] U.S. Cl. ................................. 606/144; 606/139; 112/169; 112/80.03
[58] Field of Search ............. 606/139, 144, 145, 147, 606/148, 184, 187, 205; 112/80.03, 169

[56] References Cited

U.S. PATENT DOCUMENTS

| | | |
|---|---|---|
| 1,037,864 | 9/1912 | Carlson et al. . |
| 1,449,087 | 3/1923 | Bugbee . |
| 1,822,330 | 9/1931 | Ainslie .................. 606/145 |
| 2,213,830 | 9/1940 | Anastasi ................ 606/145 |
| 2,549,731 | 4/1951 | Wattley . |
| 2,579,192 | 12/1951 | Kohl . |
| 2,601,564 | 6/1952 | Smith . |
| 2,737,954 | 3/1956 | Knapp . |
| 2,959,172 | 11/1960 | Held . |
| 3,090,386 | 5/1963 | Curtis . |
| 3,168,097 | 2/1965 | Dormia . |
| 3,470,875 | 10/1969 | Johnson . |
| 3,807,407 | 4/1974 | Schweizer . |
| 3,901,244 | 8/1975 | Schweizer ............. 606/145 |
| 3,946,740 | 3/1976 | Bassett . |
| 4,075,941 | 2/1978 | Young et al. . |
| 4,103,690 | 8/1978 | Harris . |
| 4,557,265 | 12/1985 | Andersson . |
| 4,635,638 | 1/1987 | Weintraub et al. . |
| 4,827,931 | 5/1989 | Longmore . |
| 4,830,002 | 5/1989 | Semm . |
| 4,841,885 | 6/1989 | Santino . |
| 4,852,568 | 8/1989 | Kensey . |
| 4,890,615 | 1/1990 | Caspari et al. . |
| 4,907,590 | 3/1990 | Wang et al. . |
| 4,923,461 | 5/1990 | Caspari et al. . |
| 4,957,498 | 9/1990 | Caspari et al. . |
| 5,037,433 | 8/1991 | Wilk et al. . |
| 5,047,039 | 9/1991 | Avant et al. . |
| 5,109,780 | 5/1992 | Slouf et al. . |
| 5,129,912 | 7/1992 | |
| 5,152,769 | 10/1992 | Baber . |

FOREIGN PATENT DOCUMENTS

| | | |
|---|---|---|
| 0140557 | 5/1985 | European Pat. Off. . |
| 0162960 | 4/1949 | Germany ............. 606/147 |
| 9112301 | 1/1992 | Germany . |
| 1249853 | 10/1971 | United Kingdom . |
| 2077303 | 12/1981 | United Kingdom . |
| 1093329 | 5/1984 | U.S.S.R. ............... 606/145 |

OTHER PUBLICATIONS

REMA Brochure, REMA-Medizintechnik GmbH, 1992.

Primary Examiner—Stephen C. Pellegrino
Assistant Examiner—Jeffrey A. Schmidt

[57] ABSTRACT

The present invention is directed to a surgical suture instrument specifically designed for suturing body tissues in enclosed surgical operations. The instrument includes a casing with a slot for housing a suture needle. The needle includes a first puncture end and a second manipulation end. The needle is pivotally positioned on an axis within the casing, such that the puncture end may be exposed or retracted as needed. The casing also includes equipment to manipulate the needle within the casing.

42 Claims, 3 Drawing Sheets

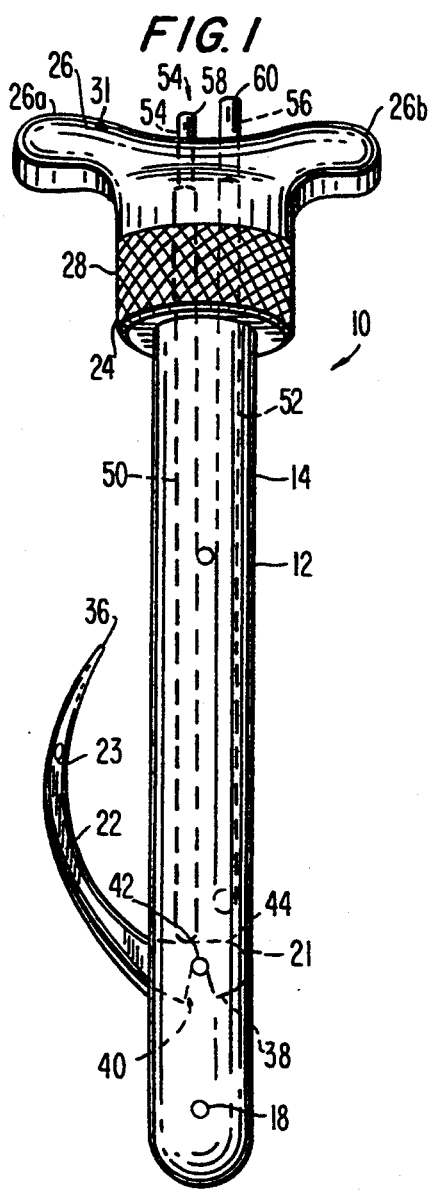
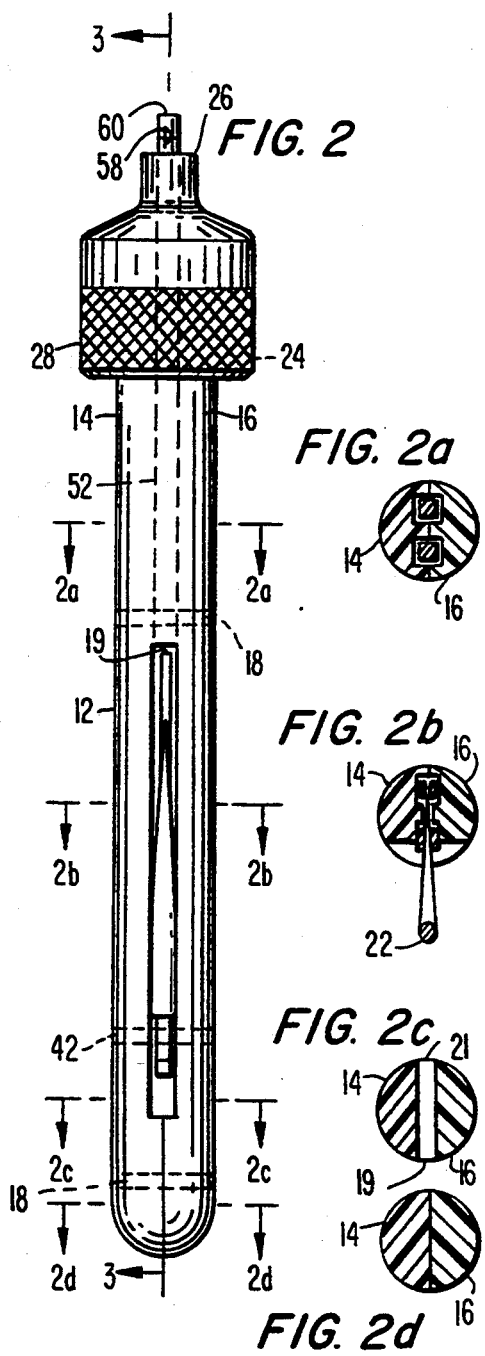

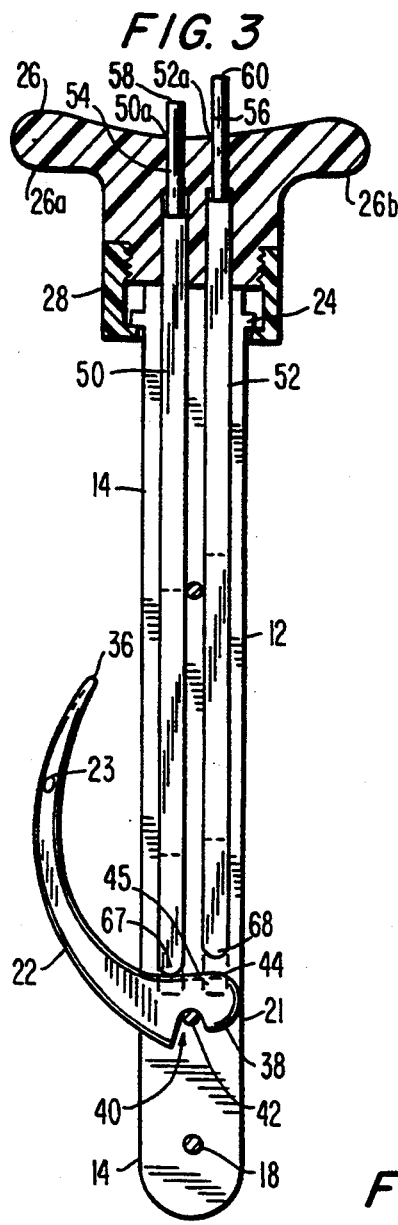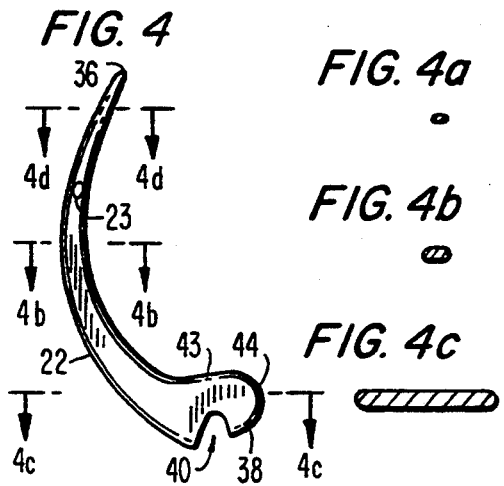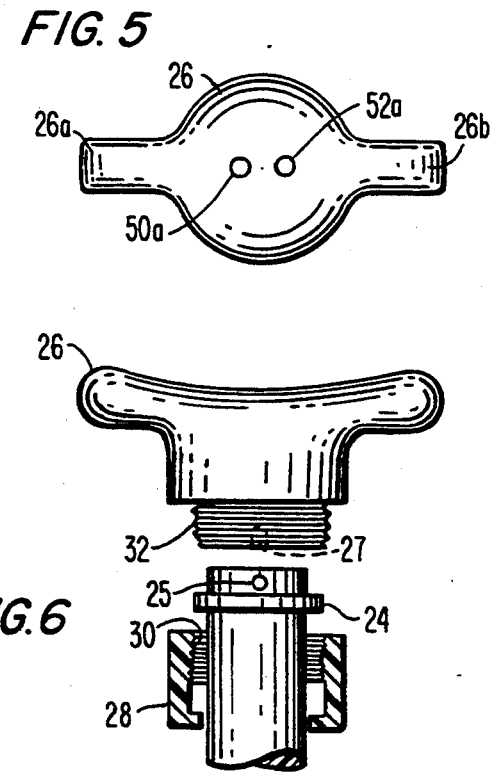

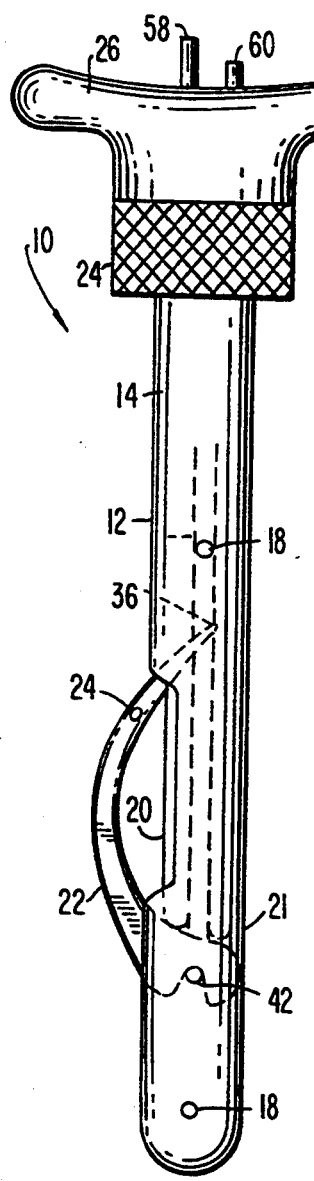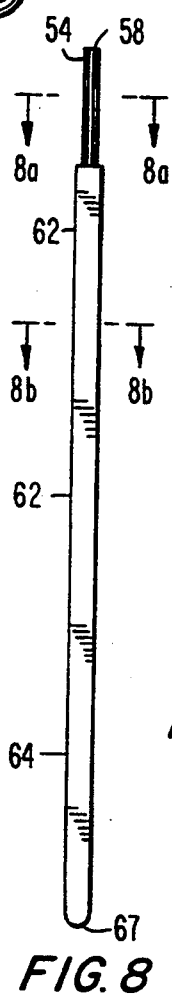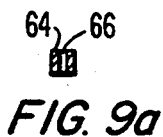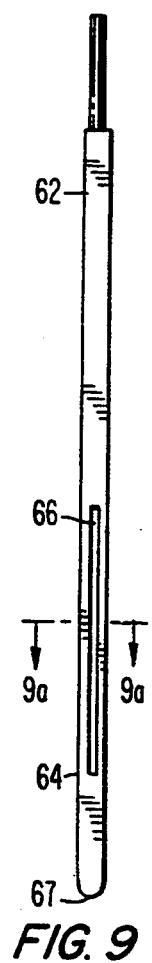
FIG. 7
FIG. 8a
FIG. 8b
FIG. 9a
FIG. 8
FIG. 9

SURGICAL APPARATUS AND METHOD FOR SUTURING BODY TISSUE

This is a continuation of application Ser. No. 07/872,212, filed on Apr. 22, 1992, now abandoned.

FIELD OF THE INVENTION

The present invention relates generally to surgical instruments. The present invention is specifically directed to a suture instrument for suturing tissue at a surgical site having limited dimensions.

DESCRIPTION OF THE PRIOR ART

For purposes of the present specification, the term "surgery" applies to a medical operation involving an incision to subcutaneous body tissue. Therefore, the surgical incision includes cutting the patient's skin, the fascia, i.e., the tough fibrous tissue which envelopes the body beneath the skin, and/or the peritoneum, i.e., the internal layer of thin connective tissue that lines the abdominal cavity and covers most of the viscera contained therein. As used herein, the term "patient" is directed toward humans, but can also include animals.

Surgical procedures can be "open" or "closed." The term "open" surgery usually describes a surgical procedure in which the surgeon accesses the surgical site by making a relatively large incision in the patient's body. For example, laparoscopic surgery involves use of a laparoscope, an illuminated optical instrument for examining internal organs. In such surgery, access must be gained to the desired body cavity. For "open" access, a relatively large incision is made at the umbilicus, the fascia is visualized, sutures are placed, and the peritoneum is opened under direct vision allowing a blunt trocar or port to be placed in the incision site. The trocar can also be fixed in position by inflatable balloons or threaded sleeves rather than suture. The trocar has a system of channels to allow the passage of various tools and carbon dioxide used to expand the abdominal cavity, i e., "pneumoperitoneum," to provide a working space and to provide a sufficient opening to view the working space by a laparoscope.

Alternatively, for "closed" access, a small incision is made and a Verres needle inserted. A Verres needle is a special needle having a spring-loaded safety tip that is designed to pierce skin, fat, fascia, and the peritoneum, without causing unwanted damage to the internal visceral organs. Carbon dioxide can then be insufflated to provide the protective pneumoperitoneum, which allows a trocar to be safely inserted. This trocar can be of the sharp pointed variety, well known to the art, or it may have a safety spring-loaded shield to protect the viscera.

The surgeon places the laparoscope through the trocar and attaches it to the camera to display the internal view on a television monitor. Once a scope is in place, other trocars or ports can be safely inserted under direct laparoscopic view at different locations to act as channels for scopes and instruments.

For example, in laparoscopic surgery directed to the gallbladder, ports, typically 10–11 mm in size, are placed at the umbilicus and in the epigastric region high in the mid-line just under the rib cage. Smaller ports (5 mm) are placed as necessary for additional instruments to accomplish the procedure. For other procedures such as appendectomies, hysterectomies, gastric, colonic or other surgeries, several ports, typically 12 mm in size, may be placed at various locations.

At the end of the procedure, the instruments and trocars are removed. If the umbilical port was placed in "open" fashion, the surgeon may have adequate room to manipulate the fascia in order to close the incision with sutures. If, however, the umbilical or other ports were placed in "closed" fashion, the skin and fascial incisions are both relatively small. There is no extra room to manipulate the fascia in order to place a closing suture, and efforts to do so are often rudimentary at best and often simply abandoned to the possible detriment of the patient.

SUMMARY OF THE INVENTION

It is therefore an object of the present invention to provide a surgical suture instrument, which can place a stitch in an incision in a restricted or "closed" surgical site.

This object is accomplished by the presently claimed invention, which is a surgical suture device comprising a casing with a slot for housing a suture needle. The needle has a puncture end and a manipulation end and is pivotally positioned within the slot such that the puncture end of the needle may be exposed or retracted within the casing. The surgical suture instrument also includes a means to manipulate the needle within the casing. Preferably, the needle is manipulated by companion manipulation rods, which are slidably positioned within channels in the casing. The manipulation rods have finger-activated ends and needle manipulation ends.

The instrument of the present invention simplifies surgical suturing processes, especially in "closed" situations, by providing a device for suturing body tissue in areas where the incision opening is tiny.

The present invention advantageously provides a simple instrument, which is easy to assemble or disassemble, can be readily sterilized and comprises few working parts. The instrument can also be conveniently formed of disposable materials. The casing also advantageously serves as an obturator to occlude the fascial and skin openings, to retain pneumoperitoneum and thus maintain direct laparoscopic vision for safe operation of the instrument. Although the instrument is specifically designed for laparoscopic surgery, it may also be used for other surgical procedures, including endoscopic surgical procedures such as arthroscopy, gastroentroscopy, and laryngobronchoscopy.

BRIEF DESCRIPTION OF THE DRAWINGS

In the drawings:

FIG. 1 is a perspective view of the surgical suture instrument of the present invention.

FIG. 2 is a side plan view of the surgical suture instrument of the present invention.

FIG. 2a is a cross-sectional view of the surgical suture instrument of FIG. 2 taken along lines 2a–2a of FIG. 2.

FIG. 2b is a cross-sectional view of the surgical suture instrument of FIG. 2 taken along lines 2b–2b of FIG. 2.

FIG. 2c is a cross-sectional view of the surgical suture instrument of FIG. 2 taken along lines 2c–2c of FIG. 2.

FIG. 2d is a cross-sectional view of the surgical suture instrument of FIG. 2 taken along lines 2d–2d.

FIG. 3 is a cross-sectional view of the surgical suture instrument of FIG. 2 taken along lines 3—3 of FIG. 2.

FIG. 4 is a side view of the suture needle of the present invention.

FIG. 4a is a cross-sectional view of the suture needle of FIG. 4 taken along lines 4a–4a.

FIG. 4b is a cross-sectional view of the suture needle of FIG. 4 taken along lines 4b–4b.

FIG. 4c is a cross-sectional view of the suture needle of FIG. 4 taken along lines 4c–4c.

FIG. 5 is a top view of the cap of the instrument of FIG. 1.

FIG. 6 is a partially exploded side view of the surgical suture instrument of the present invention.

FIG. 7 is a side view of the surgical suture instrument of the present invention illustrating the needle in retracted position.

FIG. 8 is a side view of a needle manipulation rod of the present invention.

FIG. 8a is a cross-sectional view of the needle manipulation rod of FIG. 8 taken along lines 8a–8a.

FIG. 8b is a cross-sectional view of the needle manipulation rod of FIG. 8 taken along lines 8b–8b.

FIG. 9 is a front view of a needle manipulation rod of the present invention.

FIG. 9a is a cross-sectional view of the needle manipulation rod of FIG. 9 taken along lines 9a–9a.

DETAILED DESCRIPTION OF THE DRAWINGS

Referring now to the drawings, in which like reference numerals refer to similar embodiments, reference is initially made to FIG. 1, which illustrates the surgical suture instrument of the present invention, at reference numeral 10.

Casing

The instrument 10 includes a generally tubular-shaped casing 12 of a size and configuration suitable for placement in a body opening. For purposes of the present invention, the term "body opening" is intended to include both surgically-manipulated and natural or non-surgically manipulated openings in a body cavity of a patient. Aside from its primary purpose as a suture instrument, the tubular shape of the casing also serves as an obturator to occlude the body opening. The blockage prevents the escape of any gases and enables the body opening to retain the pneumoperitoneum and to maintain direct laparoscopic vision.

The casing 12 can be made of any material known to the art and suitable for surgical applications. For example, the casing 12 may be formed of a material designed for re-use, such as stainless steel. The casing 12 can also be designed for single use and made of disposable plastics or aluminum.

Referring now to FIG. 2, the casing 12 is preferably formed of two symmetrical pieces 14, 16 which are joined together by pins, screws or the like, identified at reference numeral 18. In the case of a disposable surgical instrument 10, the pins 18 may be permanently positioned such that the pieces 14, 16 are not capable of separating. If a re-usable instrument is contemplated, the pins 18 will preferably be in the form of screws in order to allow easy separation of the pieces 14, 16 for cleaning, sterilization and repairs.

FIG. 2 illustrates pieces 14, 16 in the casing 12, which are formed to provide a pocket 19 for slidably receiving a surgical needle 22. A second pocket 21 on the opposite side of the casing 12 is provided to allow complete manipulation of the needle 22 as will be described in more detail later in the specification.

The casing 12 may also be characterized by a cutaway portion 20 as illustrated on FIG. 7. The cutaway portion 20 is adjacent the surgical suture needle 22, and is designed to provide a space for body tissue between the needle 22 and the shaft of the casing 12 in order to give the surgeon some "traction" to expose a suture opening 23 in the needle.

Cap and Coupler

The casing 12 also preferably includes a collar 24, as illustrated in FIGS. 1 and 6, for positioning an instrument cap 26 onto the surgical instrument 10. The collar 24 is designed to releasably mount a connecting coupler 28 onto the casing 12. The coupler 28 is provided with internal threads 30, which are designed to cooperate with external threads 32 on the cap 26. The assembling coupler 28 is provided to connect the cap 26 to the casing 12. The collar 24 is integrated with the casing 12 to maintain the cap 26 in position on the casing 12. Preferably, the casing 12 may be provided with a positioning button 25 on the shaft of the casing 12 above the collar 24, as illustrated in FIG. 6, to coact with a channel 27, illustrated in phantom in FIG. 6, to properly position the cap 26 on the casing 12.

As illustrated in FIG. 1, the cap 26 is preferably provided with finger grips 26a, 26b to assist the surgeon in manipulating the instrument 10. The finger grips 26a or 26b may be provided with a marker 31, e.g., a notice or other marking on one of the finger grips, to identify the position of the cut-away portion 20 and the needle 22 when the casing 12 is within a body opening.

Suture Needle

Referring now to FIGS. 1 and 3, there is illustrated the suture needle 22 of the instrument of the present invention. Preferably, the suture needle 22 is designed for single use and is therefore disposable. The needle 22 may be made of any material known to the art for use with surgical needles. Stainless steel is a preferred material, especially for reusable needles. However, disposable needles may be made of other surgical steels as tarnishing is not a problem with disposable needles. The suture needle 22 is also preferably designed in a bowed configuration, although other configurations, known to the art for surgical needles, are contemplated. The suture needle 22 is characterized by a suture opening 23 for positioning suture material. The suture opening 23 is preferably located near the puncture end 36 of the surgical needle 22. As illustrated in FIGS. 4a, 4b and 4c, the width of the needle 22 increases as the from the puncture end 36 to the needle connection end 38 opposite the puncture end 36.

The needle connection end 38 is characterized by a notch 40, which engages with an axle 42 in the casing 12 of the assembled instrument 10 to allow the suture needle 22 to pivotally rotate about the axle 42. As illustrated in the figures, the axle 42 may serve a dual purpose of providing an axle for the suture needle 22 and providing an additional pin, e.g., pins 18, for securing the pieces 14 and 16 of the casing 12. The suture needle 22 can pivotally rotate such that the puncture end 36 is exposed, as illustrated in FIGS. 1 and 3, or the puncture end 36 can be retracted within the casing 12, as illustrated in FIG. 7. The pocket 21 in the casing 12 is provided to allow full mobility to the needle 22. In either the retracted or extended position, the needle connection end 38 extends into the pocket 21, as illustrated in FIG. 7, and the rounded surface 44 remains flush with the surface of the casing 12.

The needle connection end 38 is further defined by an internal edge 43 culminating at surface 44 that is used for rotating the suture needle 22. As illustrated in FIGS. 3 and 4, the edge 43 is configured in a substantially straight-line pattern, the purpose of which will be explained later.

Needle Manipulation Rods

Positioned within the casing 12 are two parallel disposed channels 50, 52, which may be of like size and length. The channels 50, 52 are designed to retain needle manipulation rods 54, 56, which are illustrated in FIGS. 8 and 9. Referring to FIG. 5, the cap 26 is likewise provided with two channels 50a, 52a which align with the channels 50, 52, respectively when the cap 26 is placed in position on the casing 12.

As illustrated in FIG. 1, the needle manipulation rod 54 is defined by a finger-activated end 58, which extends from the channel 50. Likewise, the needle manipulation rod 56 is defined by a finger-activated end 60 protruding from channel 52a.

FIGS. 8 and 9 illustrate one of the manipulation rods, i.e., manipulation rod 54. The manipulation rods 54, 56 are further defined by a body 62, which is preferably square. It is within the scope of the present invention to provide a body 62, of any shape. However, a rounded shape is not desired as it will allow the manipulation rods 54, 56 to spin within the channels 50, 52.

The lower end of the body 62 is defined by a slotted portion 64. The slotted portion 64 provides a chamber 66 for receiving the needle 22 when the needle is in the retracted position as illustrated in FIG. 7. It is within the scope of the present invention to provide chambers 66 of the same size in each manipulation rod 54, 56. Alternatively, the chamber 66 of the manipulation rod 56 may be shorter as it only needs to accommodate the needle 22 at the area near the puncture end 36, while the chamber 66 of the manipulation rod 54 must accommodate substantially more of the needle 22 when the needle 22 retracts within the casing 12.

Located at the opposite end of the finger activated ends 58, 60 are the needle manipulation ends 67, 68 respectively. Needle manipulation ends 67, 68 are designed to coact with the edge 43 of the needle 22 to expose or retract the needle 22 according to the finger manipulations of the surgeon. In this manner the edge 43 provides a piroting surface for the rods 54, 56. For example, by fully depressing the finger-activated end 58 of the manipulation rod 54 and simultaneously releasing the finger-activated end 60 of the manipulation rod 56, the needle manipulation end 67 of the manipulation rod 54 will coact with the edge 43 of the needle 22 moving the needle 22 to the position shown in FIGS. 1 and 3 and causing the needle 22 to be exposed.

Alternatively, by depressing the finger-activated end 60 of the manipulation rod 56 and releasing the finger-activated end 58 of the manipulation rod 54, the needle manipulation end 68 of the manipulation rod 56 will coact with the edge 43 of the needle 22 to retract the needle 22 into the pocket 19 of the casing 12 and into the slots 66 of the manipulation rods 54, 56, as shown in FIG. 7.

Assembly and Disassembly

The instrument 10 is designed to be easily assembled or disassembled. To assemble the instrument 10, the pieces 14, 16 of the casing 12 are position and attached together by means of the pins 18 and the axle 42. The needle 22 is placed through the pocket 19 and positioned on the axle 42 as illustrated in FIG. 3. The manipulation rods 54, 56 are then placed in the channels 50, 52 such that the slots 66 are in proper placement and alignment with respect to the needle. The coupler 28 is slipped over the casing 12 and placed in alignment with the collar 24. The cap 26 is fitted over the manipulation rods 54, 56 such that the channels 50a, 52a in the cap coact with the channels 50, 52 in the casing 12. The coupler 28 is then threadably tightened onto the cap. Disassembly follows the opposite procedure.

Preferred Mode of Use

A preferred method of closing an umbilical incision with the surgical suture instrument 10 of the present invention will now be described. Following completion of the operative portion of the surgical procedure, the umbilical trocar is removed. A finger or blunt trocar may then be inserted into the incision site to prevent carbon dioxide gas from leaking out of the abdominal cavity.

When the suture is to be made at the umbilical body opening, the finger or blunt trocar is removed and the surgical instrument 10 is positioned in the body opening. At this point, the surgeon fully depresses the finger-activated end 60 of the manipulation rod 56 to retract the needle 22 such that the puncture end 36 is within the casing 12 as illustrated in FIG. 7. The surgical instrument 10 is then advanced into the body cavity through the body opening. When the surgeon observes that the needle 22 has passed beyond the body cavity wall, the surgeon fully depresses the finger-activated end 58 of the manipulation rod 54 to expose the puncture end 36 of the needle 22. The needle 22 is then ready to pierce the tissue wall. The instrument 10 is then retracted from the body opening. Retracting the instrument 10 from the body opening enables the puncture end 36 of the needle to penetrate the surgically-cut body tissue adjacent the body opening. The surgeon can manipulate the needle 22 by adjustably depressing the finger-activated ends 58 and 60 of the manipulation rods 54, 56. At this point, the puncture end 36 of the needle has successfully punctured the tissue.

Gentle retraction of the surgical instrument 10 allows the needle 22 exit the body opening and expose the suture opening 23. At this point, the body tissue is skewered on the needle 22.

When the suture opening 23 of the needle 22 is exposed at skin level, a suture is passed through the suture opening 23. Suture material can be any of a variety of surgical suture thread-like material known to the art. The instrument 10 is then gently reinserted in the body opening, with minimal pressure, on the manipulation rods 54, 56, allowing the needle 22 to naturally pull through its track in the tissue until the surgeon can see the full needle in the body cavity via the endoscopic camera in the other body opening. The instrument 10 is then rotated approximately 180°. The surgeon fully depresses the manipulation rod 54 to expose the needle, and the instrument 10 is withdrawn from the body opening. As before, the surgeon can balance the pressure between the manipulation rods 54, 56 in order to "sheath the tip" of the needle 22 after it has passed the body tissue and before it breaks the skin.

When the suture can be seen from outside the body opening, the thread is grasped and extracted from the suture opening 23 in the needle. The stitch is placed, but not tied. The instrument 10 is then ready for re-insertion in the body opening, in order to release the needle 22 from the tissue. Once the instrument has been reinserted in the body opening, the needle 22 is then fully sheathed by pressing the finger-activated end 60 of the manipulation rod 56 and the instrument is completely and finally removed from the body opening. The suture is tied to close the body opening.

The instrument 10 allows a safe, secure and expeditious tissue closure mechanism for small trocar incisions while maintaining adequate pneumoperitoneum and direct laparoscopic visualization.

It is understood that the invention is not confined to the particular construction and arrangement herein illustrated and described, but embraces such modified forms thereof as come within the scope of the following claims. For example, activators such as rocker switches, handles and buttons are contemplated to manipulate the needle 22.

What is claimed is:

1. A method of suturing an incision at a suture site from within a body opening the method comprising:
   a. positioning a surgical suture instrument at the suture site outside a body opening, the surgical suture instrument comprising a casing having a pocket for housing a suture needle, a needle having a puncture end, a suture opening and a manipulation end, the needle being pivotally positioned within the pocket about a pivot point being generally longitudinally fixed relative to said casing, such that the puncture end is alternately exposed or retracted within the casing, and means associated with the manipulation end of the suture needle and operable from a proximal end of the instrument casing for manipulating the needle within the casing;
   b. retracting the needle such that the puncture end is within the casing;
   c. advancing the casing of the surgical instrument into the body opening;
   d. exposing the puncture end of the needle;
   e. piercing the tissue surrounding an interior portion of the body opening with the needle at a defined site;
   f. retracting the surgical instrument from the body opening to enable the puncture end of the needle to penetrate the body tissue such that the needle exits the body opening and exposes the suture opening;
   g. passing a suture thread through the suture opening;
   h. reinserting the surgical instrument;
   i. rotating the surgical instrument approximately 180°;
   j. exposing the needle;
   k. withdrawing the surgical instrument from the body opening to enable the puncture end of the needle to penetrate the body tissue such that the needle exits the body opening and exposes the suture opening which suture opening includes the previously threaded suture;
   l. fixing the suture thread outside the body opening;
   m. releasing the needle from the tissue;
   n. removing the surgical instrument from the body opening.

2. A surgical suture instrument, comprising:
   a. a casing comprising a pocket for housing a suture needle;
   b. a suture needle having a puncture end and a manipulation end, the suture needle being pivotally positioned within the pocket about a pivot point being generally longitudinally fixed relative to said casing, such that the puncture end is alternately exposed to permit penetration of tissue or retracted within the casing to prevent penetration of tissue; and
   c. means associated with the manipulation end of the suture needle and operable from a proximal end portion of the instrument casing for manipulating the suture needle between a retracted position and an exposed position whereby the needle is pivoted outwardly away from the casing.

3. The suture instrument of claim 2 wherein the casing comprises two pieces joined together.

4. The suture instrument of claim 2 wherein the casing is configured and dimensioned sufficient such that upon insertion of the instrument into a body opening the body opening becomes occluded.

5. The suture instrument of claim 2 comprising disposable component parts.

6. The suture instrument of claim 2 wherein the casing further includes first and second axially positioned channels, the casing further comprising first and second needle manipulation rods slidably positioned within the first and second channels of the casing respectively, the first and second needle manipulation rods each having a finger-activated end and a needle manipulation end, wherein the first needle manipulation rod comprises means to retract the puncture end of the needle and the second needle manipulation rod comprises means to expose the puncture end of the needle.

7. The suture instrument of claim 6 wherein the needle manipulation rods include a structure which prevents rotation of the manipulation rods within the channels.

8. The suture instrument of claim 6 wherein the needle manipulation rods are slotted to receive the puncture end of the suture needle when the suture needle is retracted.

9. The suture instrument of claim 6 wherein the casing includes an open end and a closed end, wherein the open end comprises a cap for maintaining the needle manipulation rods in the casing, the cap being provided with openings for exposing the finger manipulation ends of the manipulation rods.

10. The suture instrument of claim 9 wherein the openings of the cap are axially aligned with the first and second channels in the casing.

11. The suture instrument of claim 10 wherein the casing comprises a collar for positioning the cap on the casing.

12. The suture instrument of claim 10 wherein the cap further comprises finger grips.

13. The suture instrument of claim 2 comprising an axle for pivotally positioning the suture needle.

14. A surgical instrument, for closing a trocar incision, which comprises:
   an elongated housing having at least one longitudinal pocket having an opening spaced from a distal end of said elongated housing thereof, said elongated housing having an outer surface of substantially uniform cross-sectional diameter along the length thereof which is adjacent said longitudinal pocket opening;
   a needle deployably attached to said elongated housing; and
   movable means associated with said housing, engageable with said needle, for openably deploying said needle between a first position substantially within said pocket and a second position outwardly spaced from said elongated housing such that said needle is moved outwardly away from said elongated housing.

15. Apparatus for closing a trocar incision according to claim 14 wherein said needle is arcuate.

16. Apparatus for closing a trocar incision according to claim 14 wherein when said needle is in said second position said needle is spaced from said pocket in substantially the same transverse plane therewith.

17. Apparatus for closing a trocar incision according to claim 14 wherein said movable means are distally movable.

18. Apparatus for closing a trocar incision according to claim 17 wherein said movable means comprises at least one rod slidably mounted within said housing.

19. A surgical instrument, for closing a body cavity incision, which comprises:
an elongated housing having a proximal end and a distal end;
a needle having a puncture end;
means associated with said elongated housing for deployably attaching said needle to said elongated housing, such that upon deployment of said needle, said puncture end is directed toward said proximal end of said elongated housing; and
means disposed within said housing for operably deploying said needle from a first position to a second position spaced from said housing.

20. A surgical instrument for closing a body cavity incision according to claim 19 wherein said attaching means comprises a pivot mounted within said elongated housing such that said needle is pivotable about said pivot.

21. A surgical instrument for closing a body cavity incision according to claim 20 wherein said pivot is generally longitudinally fixed relative to said elongated housing.

22. A surgical instrument for closing a body cavity incision according to claim 19 wherein said attaching means comprises at least one rod slidably mounted within said housing.

23. A surgical instrument for closing a body cavity incision according to claim 19 wherein when said needle is in said second position said at least one needle is spaced from said pocket in substantially the same transverse plane therewith.

24. Apparatus, for closing a trocar incision, which comprises:
an elongated housing having at least one longitudinal pocket which defines an opening;
a needle having a puncture portion and a manipulation portion, said needle being deployably mounted within said pocket of said elongated housing portion such that said manipulation portion generally extends along a plane extending generally perpendicular to a longitudinal axis of said apparatus; and
an actuator operatively associated with said needle, said actuator operably deploying said needle such that said needle is moved outwardly away from said elongated housing and said manipulation portion of said needle remains substantially within said plane.

25. Apparatus for closing a trocar incision according to claim 24 wherein said needle is deployably mounted within said pocket of said elongated housing whereby said needle is pivotable between a first position and a second position.

26. Apparatus for closing a trocar incision according to claim 24 wherein said actuator comprises at least one rod slidably disposed within said elongated housing.

27. Apparatus for closing a trocar incision according to claim 24 wherein said needle is arcuate.

28. Apparatus for closing a trocar incision according to claim 24 wherein said needle is oriented with said puncture end portion directed toward a proximal end of said elongated housing.

29. A surgical instrument, for closing a trocar incision, which comprises:
an elongated housing having a distal end;
a needle deployably mounted on said elongated housing, said needle having a puncture end portion such that said needle is oriented with said puncture end portion directed toward a proximal end of said elongated housing; and
an actuator disposed at least partially within said housing, said actuator distally movable to operably deploy said needle between a first position and a second position outwardly spaced from said elongated housing such that said needle is moved outwardly away from said elongated housing upon distal movement of said actuator.

30. A surgical instrument for closing a trocar incision according to claim 29 wherein said needle is arcuate.

31. A laparoscopic surgical instrument, for closing a trocar incision, which comprises:
an elongated housing having a proximal end portion and a distal end portion;
a needle deployably mounted adjacent said distal end; and
an actuator associated with said elongated housing, said actuator moveable between a first position spaced from said needle and a second position in engagement with said needle, to operably deploy said needle alternately between a first position to prevent penetration of tissue and a second position outwardly spaced from said elongated housing such that said needle is moved outwardly away from said elongated housing to permit penetration of tissue.

32. A laparoscopic surgical instrument for closing a trocar incision according to claim 31 wherein said needle is arcuate.

33. A laparoscopic surgical instrument for closing a trocar incision according to claim 31 wherein said elongated housing includes at least one longitudinal pocket said pocket defining an opening which lies along a first plane which is normal to a radial plane of said elongated housing and wherein when said needle is in said second position, said needle is spaced from said pocket in a second plane which is transverse to said first plane of said pocket opening.

34. A laparoscopic surgical instrument for closing a trocar incision according to claim 31 wherein said needle includes a puncture end portion such that said needle is oriented with said puncture end portion directed toward said proximal end of said elongated housing.

35. A method for closing a trocar incision, the method comprising the steps of:
(a) providing a suturing instrument having:
an elongated housing,
a needle operatively associated with said housing;
means for deployably mounting said needle such that at least a portion of said needle remains longitudinally fixed relative to said elongated housing during deployment; and means disposed at least partially within said housing, for operably deploying said needle between an initial position and a deployed position away from said housing;

b) inserting said suturing instrument into an exterior opening of a trocar incision formed in a patient's body;

(c) deploying, at a predetermined position, said needle from said initial position to said deployed position; and (d) moving said deployed needle toward said exterior opening of said incision, from within said incision.

36. A laparoscopic surgical instrument comprising:

an elongated housing having a proximal end and a distal end;

a needle having a puncture portion;

means for mounting said needle adjacent said distal end of said elongated housing for movement between a first position wherein said puncture portion is disposed within said elongated housing and a second position wherein said puncture portion is spaced from said elongated housing to permit penetration of tissue; and means for moving said needle alternately between said first and second positions, said moving means movable from a disengaged position to an engaged position with said needle to move said needle to said second position.

37. A surgical suture instrument, comprising:

a. an elongated housing having a pocket;

b. a suture needle having a puncture end and a manipulation end, the puncture end being positionable within the pocket, said needle being pivotally positioned about a pivot fixed longitudinally relative to said elongated housing such that the puncture end is pivotable between an exposed position to permit penetration of tissue and a retracted position within said elongated housing to prevent penetration of tissue; and c. means spaced from the puncture end of the suture needle and operable from a proximal end portion of said elongated housing for deploying said puncture end of the suture needle between said retracted position and said exposed position whereby the needle is pivoted outwardly away from the pocket.

38. A surgical suture instrument, comprising:

a. an elongated housing having a pocket;

b. a suture needle having a puncture end and a manipulation end, being mounted to said elongated housing, such that the puncture end is pivotally movable between an exposed position to permit penetration of tissue and a tethered position within the elongated housing to prevent penetration of tissue; and c. a deployment member operatively associated with said suture needle such that distal movement of said deployment member pivots said suture needle to said exposed position.

39. A surgical suture instrument, comprising:

a. an elongated housing having a pocket;

b. a suture needle consisting of a C-shaped structure and having a puncture end and a manipulation end, said needle being deployable between first and second positions; and c. means operable from a proximal end of the elongated housing for manipulating the suture needle between said first position and said second position whereby the suture needle is pivoted outwardly away from said elongated housing.

40. A surgical suture instrument according to claim 39, wherein said puncture end of said C-shaped suture needle is positioned proximal of a distal end of said suture instrument.

41. A surgical suture instrument according to claim 39, wherein said puncture end of said C-shaped suture needle is oriented toward said proximal end of said instrument when said C-shaped suture needle is in said first position.

42. A surgical suture instrument according to claim 39, wherein said puncture end of said C-shaped suture needle is oriented toward said proximal end of said instrument when said C-shaped suture needle is in said second position.

* * * * *